United States Patent [19]

Pierantozzi

[11] Patent Number: 4,760,184

[45] Date of Patent: Jul. 26, 1988

[54] ALKYLATION OF AROMATIC AMINES IN THE PRESENCE OF NON-ZEOLITIC MOLECULAR SIEVES

[75] Inventor: Ronald Pierantozzi, Orefield, Pa.

[73] Assignee: Air Products and Chemicals, Inc., Allentown, Pa.

[21] Appl. No.: 862,088

[22] Filed: May 12, 1986

[51] Int. Cl.$^4$ ............................................. C07C 85/24
[52] U.S. Cl. ................................. 564/409; 564/315; 564/330; 558/376; 560/43
[58] Field of Search ...................... 564/409, 315, 330; 558/376; 560/43

[56] References Cited

U.S. PATENT DOCUMENTS

| | | | |
|---|---|---|---|
| 2,762,845 | 9/1956 | Stroh et al. | 260/578 |
| 3,201,486 | 8/1965 | Bielawski et al. | 260/671 |
| 3,275,690 | 9/1966 | Stroh et al. | 260/576 |
| 3,649,693 | 3/1972 | Napolitano | 260/578 |
| 3,923,892 | 12/1975 | Klopfer | 260/578 |
| 4,310,440 | 1/1982 | Wilson et al. | 252/435 |
| 4,440,871 | 7/1982 | Lok et al. | 502/214 |
| 4,499,315 | 2/1985 | Garska et al. | 585/415 |
| 4,499,316 | 2/1985 | Garska et al. | 585/415 |
| 4,527,001 | 7/1985 | Kaiser | 585/643 |
| 4,554,143 | 11/1985 | Messina et al. | 585/660 |

FOREIGN PATENT DOCUMENTS

| | | |
|---|---|---|
| 0121232 | 10/1984 | European Pat. Off. |
| 0124119 | 11/1984 | European Pat. Off. |
| 0132708 | 2/1985 | European Pat. Off. |
| 1051271 | 2/1959 | Fed. Rep. of Germany |
| 1406739 | 6/1965 | France |
| 56-110652 | 9/1981 | Japan |
| 414574 | 8/1934 | United Kingdom |
| 846226 | 8/1960 | United Kingdom |

Primary Examiner—Glennon H. Hollrah
Assistant Examiner—John A. Sopp
Attorney, Agent, or Firm—Mark L. Rodgers; William F. Marsh; James C. Simmons

[57] ABSTRACT

This invention relates to a process for producing ring alkylated aromatic amines. In accordance with this process an aromatic amine is reacted with an olefin, diolefin or an alcohol using a non-zeolitic molecular sieve as a catalyst. Under the conditions of the process the catalyst is extremely active, and with aromatic amines that are capable of alkylation at the ortho and para positions, high selectivity to the ortho alkylated isomer can be achieved.

16 Claims, No Drawings

ALKYLATION OF AROMATIC AMINES IN THE PRESENCE OF NON-ZEOLITIC MOLECULAR SIEVES

TECHNICAL FIELD

This invention pertains to a process for alkylating aromatic amines in the presence of non-zeolitic, molecular sieves. In a preferred embodiment the process provides for the production of a reaction product wherein the ratio of ortho-alkylated aromatic amine to para-alkylated aromatic amine is high.

BACKGROUND OF THE INVENTION

Processes for alkylating a variety of alkylatable aromatic compounds by contacting such compounds with a hydrocarbon radical providing source such as an olefin or alcohol are widely known. Typically, alkylatable aromatic compounds are mononuclear aromatic compounds themselves or those substituted with a hydroxyl, amine or an ether group. The alkylation has been carried out in the presence of homogeneous and heterogeneous catalyst systems.

Ring alkylated aromatic amines have been some of the products produced by alkylation procedures. Ring alkylated aromatic amines have a variety of uses in chemical synthesis. Some of the early uses were intermediates for substituted isocyanates, herbicidal compositions, dyestuffs and textile auxiliary agents. More recently aromatic amines have been utilized as chain lengthening or cross-linking components in polyurethane systems. These are commonly referred to as chain extenders.

Representative references which illustrate some of the early processes in forming ring alkylated aromatic amines are:

British Pat. No. 414,574 discloses the reaction of aniline with various olefins, e.g., cyclohexene and alcohols, e.g., butanol in the presence of a neutral or weakly acidc catalyst system commonly referred to as hydrosilicates at temperatures from 200°–270° C. Ortho and para-cyclohexylaniline, N-cyclohexylaniline, N-butylaniline and para-methyl-ortho-cyclohexylaniline and N-cyclohexyl-para-toluidine are listed as representative products.

British Pat. No. 846,226 discloses ring alkylation of aromatic amines with olefins using active, substantially neutral bleaching earths of the montmorillonite type as a catalyst.

German Pat. No. 1,051,271 discloses the ring alkylation of aniline with an olefin, e.g., ethylene, in the presence of kaolin or in the presence of aluminum and aluminum alloys. Alkylation with higher olefins, e.g., propylene, butylene, etc., was carried out in the presence of Friedel-Crafts catalysts or bleaching earths under liquid phase conditions at temperatures from 150°–350° C. Examples of catalytic systems included aluminum chloride, zinc chloride, boron trifluoride, sulfuric acid, phosphoric acid and bleaching earth. Ring alkylation at the ortho-positions was predominant, although other products such as the di and tri-alkylated aniline product were produced.

In an article by Zollner and Marton, Acta Chim. Hung. Tomus 20, 1959 (Pages 321–329) the vapor phase alkylation of aniline with ethanol was effected in the presence of aluminum oxide.

U.S. Pat. Nos. 3,649,693 and 3,923,892 disclose the preparation of ring alkylated aromatic amines by reacting an aromatic amine with an olefin in the presence of aluminum aniline, optionally including a Friedel-Crafts promoter. Reaction products included 2-ethylaniline, and 2,6-diethylaniline.

Stroh, et al., in U.S. Pat. Nos. 3,275,690; 2,762,845, Japanese No. SHO 56-110652, and, as mentioned previously, AS No. 1,051,271, disclose various processes for preparing alkylated aromatic amines by reacting an aromatic amine with an olefin in the presence of Friedel-Crafts catalysts as well as a combination of the Friedel-Crafts catalysts in the presence of halogen compounds combined with aluminum. Representative reaction products included 2-cyclohexylaniline, diethyltoluenediamine, diethylaniline, diisopropylaniline and mono-tert-butylaniline.

The art, e.g., Netherlands Application No. 6,407,636 has recognized that alkylation of various aromatic and heterocyclic compounds can be carried out in the presence of a zeolite having a port size greater than 6 Angstroms wherein active cationic sites are obtained with exchangeable metal or hydrogen cations in their ordered internal structure.

French Pat. No. 1,406,739, which is equivalent to Netherlands Application No. 6,407,636, discloses the preparation of alkylated aromatic compounds having polar substitutions thereon utilizing alumino-silicates having a pore size of at least 6 Angstroms as a catalyst. Cations of low valence were deemed to have been particularly effective for the ring alkylation of aromatic compounds having weakly basic substituents such as aromatic amines. The examples show the alkylation of aniline with propylene in the presence of a sodium zeolite X and alkylation of diphenylamine with propylene in the presence of a molecular sieve 13X which has undergone a partial exchange with rare earths and having a pore size of 7–8 Angstroms.

U.S. Pat. No. 3,201,486 discloses processes for alkylating various aromatic hydrocarbons with an olefin using sulfuric acid and hydrogen fluoride as a catalyst. In the particular reference solid phosphoric acid was used as the catalyst.

Although the prior art has disclosed that a variety of catalytic systems can be utilised in the alkylation of aromatic hydrocarbons and aromatic amines, the art also teaches that a variety of reaction products are produced, including both ortho and para-isomers of mononuclear aromatic amines as well as, mono, di and tri alkyl substituted amines. In addition the prior art teaches that neutral to weakly acidic catalysts are preferred for effecting ring alkylation of the aromatic amines. Even though the prior art has suggested preferred catalytic system such systems also involve batch, liquid phase operation which may be difficult to operate over an extended period of time, and tend to give more para product. In addition, many of the processes suffer from poor conversion, poor reaction rate and an inability to produce high ortho to para isomer ratios at high conversion.

U.S. Pat. No. 4,310,440 describes a novel class of molecular sieve materials. These materials are aluminophosphates (ALPO's) and consist of alternating tetrahedra of Al and P. The tetrahedra are linked together in such a way as to provide microporus crystalline structure to the material. These materials are best described as non-zeolitic molecular sieve materials. Although the structures of some of the ALPO compositions are analogous to the known zeolite materials, several novel structures within this class of materials have been identified.

Other new materials based on the aluminophosphate family of molecular sieves have been described and patented in numerous U.S. and E.P. patents and patent applications. For example, U.S. Pat. No. 4,440,871 describes a member of the class of aluminophosphates that are generated by the substitution of Si for Al or P into the ALPO structure. These silicoaluminophosphates (SAPO's) have ion exchange properties formed by the substitution of the tetravalent Si for the trivalent Al or pentavalent P. These materials when exchanged with protons exhibit the protonic acidities normally observed for zeolites. Likewise, other materials in this class containing Ti, Cr, B, Mg, Co, and other metallic component substituted for Al and P have been prepared and described in the following patents: EP No. 121232 (TAPO's), EP No. 132708 (metalloaluminophosphates, MeAPO's), EP No. 131946 (FAPO's).

The use of these materials in hydrocarbon and alcohol conversion processes is described in several patents issued to Union Carbide Corporation. U.S. Pat. No. 4,499,316 describes the use of ALPO's in the conversion of olefins to aromatic hydrocarbons. EP No. 124119 describes compositions containing SAPO's for the conversion of petroleum feedstocks to lighter fractions, i.e. hydrocracking. U.S. Pat. No. 4,527,001 describes the use of non-zeolitic crystalline molecular sieves of this class as catalysts for the interconversion of light olefins. U.S. Pat. No. 4,499,315 describes the conversion of hydrocarbons to aromatics using SAPO materials as a catalyst. U.S. Pat. No. 4,499,316 describes the use of ALPO's for a similar conversion process.

SUMMARY OF THE INVENTION

The present invention is a process for alkylating aromatic amines by reacting said aromatic amines with an alcohol, olefin or diolefin. The reaction is run under reaction conditions suitable for carrying out said alkylation, and in the presence of a non-zeolitic, molecular sieve catalyst. The non-zeolitic, molecular sieve catalysts are of the alumionphosphate class; i.e. ALPO, MeAPO, SAPO, etc. in crystalline form having micropores sufficiently large to allow the reactants to diffuse into said micropores and products to diffuse out.

Use of these aluminophosphate class of catalysts in this type of alkylation reaction allows for high selectivity of ortho alkylates relative to para and N-alkylates. The activity of the catalysts provide for high conversions and high rates of ring alkylation. Additionally, the catalysts can be utilized in a fixed bed catalytic reactor for continuous vapor or liquid phase operation.

DETAILED DESCRIPTION OF THE INVENTION

The present invention is a process for alkylating an aromatic monoamine or diamine by reacting said aromatic monoamine or diamine with an alcohol, an olefin or a diolefin, under reaction conditions suitable for carrying out the alkylation. The alkylation reaction is carried out in the presence of a non-zeolite, molecular sieve catalyst having a microporus structure wherein the micropores are sufficiently large to allow the reactants and products to diffuse into and out of said micropores.

The aromatic amines useful in this process can be represented by the formulas:

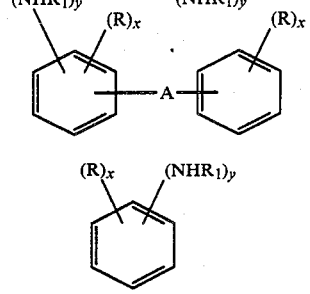

where R is hydrogen, $C_{1-10}$ alkyl or halogen, phenyl, alkoxy, ester, or nitrile; $R_1$ is hydrogen or $C_{1-10}$ alkyl; X is 1 or 2, A is $C_{0-4}$ alkylene or NH, y is 1 or 2 except one y in formula I can be zero.

As shown in the above formulas, the aromatic amine can be monoamino or diamino substituted on the aromatic ring. Further, the aromatic amine can be substituted with a variety of substituents which are nonreactive with the olefin or alcohol in the alkylation reaction. Examples of nonreactive substituents include alkylamino where the alkyl portion has from 1–6 carbon atoms, such as N-ethyl, N-propyl and N-tert-butyl, alkyl where the alkyl substituent has from 1–6 carbon atoms, e.g. ethyl, propyl, tert-butyl and cyclohexyl, methylcyclohexyl; alkoxy where the carbon content is from 2–6 carbon atoms, and ester, where the carbon content is from 2–6 carbon atoms.

Many of the amines included within the formulas I and II have hydrogen atoms which are reactive in both the ortho and para positions to the amino group. When both of these hydrogens are reactive to alkylation, one has the ability to selectively produce one isomer in favor of another. Typically, in the case of aromatic amines which have hydrogen atoms which are reactive in both positions the para position is more thermodynamically stable. In most of the prior art systems, one could not simultaneously obtain high conversion of aromatic amine and high selectivity to an ortho-alkylated amine. If one went to high conversion of aromatic amine, one obtained higher percentages of the more stable para-isomer. Typically, low conversions, e.g., 20% to 30% were required to achieve a high production of ortho-isomer, e.g., an ortho-para isomer molar ratio of 3 or greater to 1.

Specific examples of aromatic amines suited for alkylation, including those with active hydrogens in positions ortho and para to the amino group, include aniline, toluidine, xylidene, toluenediamine, xylidenediamine, diphenylamine, methylenedianiline, N-ethyl aniline, N-propyl aniline, (N-propylamino)aminotoluene, isobutylaniline, phenyl aniline, phenylenediamine and methylbenzylaniline.

Alkylating agents used for practicing the invention are mono- and di-aliphatic, acyclic and cyclic $C_2$–$C_{10}$ olefins and diolefins such as ethylene, propylene, butene isobutylene, isoamylene, cyclohexene, 1-methylcyclohexene, 1-methylcyclopentene, butadiene, cyclopentadiene, cyclohexadiene and halogenated derivatives. Typically, these olefins will have from 2 to 10 carbon atoms in the structure. Although olefins are often preferred, in many instances other materials can be substituted as alkylating agents; e.g., $C_2$–$C_{10}$ paraffin alcohols such as methanol, ethanol, propanol, etc. While alkyl halides such as ethyl chloride, propyl bromide, etc. can be used, they generally are not suited for the ortho-alkylation of aromatic amines because the acidity of these alkylating agents tend to interfere with the selectivity of the reaction. It was found that in some cases where paraffin alcohols are employed, the water from the reaction system tends to reduce the ability of the aromatic amine to ring alkylate and when useful alkylation conditions, e.g., temperature, are achieved the product formed often contains a higher proportion of the para-isomer than when using the corresponding olefin.

In the alkylation of aromatic amines, the molar ratio of olefin to aromatic amine influences the selectivity of the reaction. In those cases where the aromatic amine can be alkylated in the ortho and para positions, the molar ratio of olefin to aromatic amine influences, to some degree, whether the ring alkylation is ortho to the amine or para to the amine. Typically olefin to amine molar ratios will range from about 1 to 20 moles olefin per mole of aromatic amine and preferably 2–8 moles olefin per mole of aromatic amine. The utilization of higher mole ratios of olefin to aromatic amine tends to increase the amount of ortho-alkylated product produced.

Catalysts used in the reaction of the present invention are non-zeolitic, molecular sieves, and more specifically are crystalline aluminophosphates, silicoaluminophosphates, magnesium aluminophosphates, and others of the metallo-aluminophosphate class. The term "non-zeolitic" is used herein to denominate molecular sieves which are not formed of an essential framework of only aluminum and silicon tetrahedra such as the essential framework present in ZSM-type zeolites, zeolites Y and X and the like. A detailed definition and examples of "non-zeolitic" molecular sieves can be found in EP Patent Application No. 124,119. These catalysts have a three-dimensional microporous crystal framework structure of $PO_2+$ and $AlO_2-$ tetrahedral units with substitution by other atoms possible. The crystalline structure imparts microporosity to the catalysts which are believed to serve as the reactive sites for the reaction. The micropores therefore, must be sufficiently large to allow the reactants to diffuse into the micropores when the alkylation takes place and for the reaction products to diffuse out of the pores. An average micropore size of about 6 angstroms as measured by absorption of probe molecules is usually sufficient, with an average of at least 7 angstroms being preferred. The micropores of each structure have generally uniform molecular dimensions, with very little deviation among pores of the same structure. Catalysts can also be impregnated with metals of Groups 1 to 15 of the Periodic Table.

A detailed description of the crystalline aluminophosphates and silicoaluminophosphates which are used to catalyze the present reaction are described in detail in U.S. Pat. No. 4,440,871, assigned to Union Carbide Corporation, Danbury, CT. Preparation and structure of a large number of these materials are disclosed. Several of the materials useful for catalyzing the present invention, along with their corresponding pore sizes (diameters), are listed in Table 1 below.

TABLE 1

| Composition | Pore Size* (Å) |
| --- | --- |
| SAPO-5 | 8 |
| SAPO-11 | 6 |
| SAPO-31 | ~7 |
| SAPO-37 | 8 |

TABLE 1-continued

| Composition | Pore Size* (Å) |
| --- | --- |
| SAPO-40 | ~7 |
| SAPO-41 | 6 |
| ALPO-5 | 8 |
| ALPO-11 | 6 |
| MeAPO-36 | 6 |

*As measured by absorption of probe molecules.

The alkylation of aromatic amines to effect ring alkylation of the aromatic amine can be carried out in a fixed bed reactor with the reactants being fed downflow or upflow through the reactor. The reaction can also be carried out in a stirred autoclave or a recycle reactor. Temperatures from 25° C. to 350° C. and pressure of from 14.7 to 2000 psia are utilized. Although conversion of an aromatic amine to a ring alkylated product may be greater at temperatures near the upper end of the range specified, the degree of alkylation in the ortho-position as opposed to the para-position may be greatly reduced and olefin polymerization may occur. Higher conversions obtained at high temperatures tend to form higher concentrations of the para-isomer. Thus, to obtain a reaction product with the highest ortho to para-isomer ratio the reaction temperature is controlled to produce a conversion range that will give the highest ortho to para-isomer ratio. For ethylene that temperature will probably be greater than the reaction temperature for propylene, the propylene temperature will be greater than for isobutylene. One of the advantages of using the ALPO, SAPO, or MeAPO catalysts is that high conversions can be achieved at lower temperatures and that these lower temperatures for alkylation permit high selectivity for ortho-isomer away from para-products and polymer.

Pressure has some effect on the selectivity to ortho-alkylated product but its effect is much less significant than temperature. Typically pressures used in the operation will range from 14.7 to 2000 psia, with pressures of from 500 to 1,000 psia being preferred.

Liquid phase or vapor phase conditions may be utilized in the practice of the invention and the process may be carried out on a batch or continuous basis. When a batch process is utilized the proportion of aromatic amine is from about 10 to 100 weight parts per weight part catalyst.

The following examples are provided to illustrate various embodiments of the invention and are not intended to restrict the scope thereof.

Catalyst Preparation

The non-zeolitic molecular sieve catalysts of the present invention were prepared by hydrothermal synthesis from gels containing $Al_2O_3$, phosphoric acid, a templating agent and in the case of SAPO's, $SiO_2$ or a metal oxide for synthesis of MeAPO's. The synthesis is discussed in detail in U.S. Pat. Nos. 4,310,440; 4,440,871 and EP132708.

Experimental

Reactor studies were carried out by first saturating the catalyst bed with an aromatic amine and subsequently contacting it with an olefin or alcohol. Once feed flow conditions were established, the reactor temperature was raised to 250° C. at 2°/min. Product analysis was conducted by capillary gas chromatography.

Definition of Terms

Activity = first order rate constant $(K) = -(\ln(1-x) \cdot LHSV)$ where $x$ = fractional conversion LHSV = liquid hourly space velocity in moles aromatic amine/cc cat-h $$\text{Selectivity} = \frac{\text{mole product } i}{\sum\limits_{i} \text{product}} \times 100\%$$

o-alk = 2-isopropylaniline + 2,6-diisopropylaniline
p-alk = 4-isopropylaniline + 2,4-diisopropylaniline
    + 2,4,6-triisopropylaniline
N-alk = N-isopropylaniline + N,2-diisopropylaniline

EXAMPLE 1

(Comparative)

LZY82, a steam stabilized HY zeolite, was activated by heating at 95° C. for 4 hrs. then 2°/min to 400° C. and holding for 4 hrs. After cooling to room temperature, reaction conditions were established by establishing aniline flow in the catalyst bed, followed by propylene flow and a slow heating to 250° C. at 2 /min. The reaction data is summarized in Table 2 below.

TABLE 2

| Alkylation of Aniline with Propylene over HY (Comparative LZY82) Activated to 400° C. | | | | | | | | |
|---|---|---|---|---|---|---|---|---|
| Temp | P | | LHSV × | | SELECTIVITY (mole %) | | | Activity × |
| (°C.) | (psig) | N/R* | 10³ | Conv | N—Alk | o-Alk | p-Alk | 10³ |
| 252 | 822 | 0.20 | 2.74 | 91.4 | 18.0 | 68.8 | 12.1 | 6.59 |
| 249 | 812 | 0.20 | 2.74 | 92.1 | 18.5 | 68.5 | 11.8 | 6.91 |

*aniline/propylene molar ratio

EXAMPLE 2

The catalyst SAPO-37 (vol = 7.96 cc, wt = 3.288 g) was activated by first heating to 95° C. for 4 hrs., then heating to 400° C. at 2°/min and holding for 4 hrs. After cooling to room temperature, reaction conditions were established by establishing aniline flow in the catalyst bed, then propylene flow and a slow heating to 250° C. at 2°/min.

The data for this example is summarized in Table 3 below.

TABLE 3

| Alkylation of Aniline with Propylene over SAPO-37 Activated to 400° C. | | | | | | | | |
|---|---|---|---|---|---|---|---|---|
| Temp | P | | LHSV × | | SELECTIVITY (mole %) | | | Activity × |
| (°C.) | (psig) | N/R | 10³ | Conv | N—Alk | o-Alk | p-Alk | 10³ |
| 249 | 961 | 0.20 | 2.74 | 93.4 | 21.4 | 63.7 | 12.1 | 7.28 |
| 247 | 961 | 0.20 | 2.74 | 94.4 | 20.9 | 64.5 | 11.9 | 7.89 |
| 248 | 967 | 0.20 | 2.74 | 94.4 | 20.6 | 61.6 | 11.3 | 7.89 |

As can be seen from a comparison of the results of the alkylation reaction using the HY zeolite with the results using the non-zeolitic SAPO-37, the SAPO-37 is about 15% more active when treated by the same activation procedure.

EXAMPLE 3

The same batch of SAPO-37 used in Example 2 was activated to 667° C. by the following temperature program:

Ambient to 242° C. at 2° C./min—hold for 2 hrs.
242 to 485 at 2° C./min hold
485–605 at 0.2°/min
605–667 at 2° C./min Reactor conditions were established as in Examples 1 and 2 above. Reactor data is reported in Table 4 below:

TABLE 4

| Alkylation of Aniline with Propylene over SAPO-37 Activated to 667° C. | | | | | | | | |
|---|---|---|---|---|---|---|---|---|
| Temp | P | | LHSV × | | SELECTIVITY (mole %) | | | Activity × |
| (°C.) | (psig) | N/R | 10³ | Conv | N—Alk | o-Alk | p-Alk | 10³ |
| 250 | 978 | 0.20 | 3.83 | 80.9 | 25.4 | 65.0 | 8.6 | 6.34 |
| 251 | 850 | 0.20 | 3.83 | 77.2 | 26.0 | 65.1 | 8.2 | 5.66 |

As can be seen from Table 4 above, the activity of SAPO-37, while still being sufficient to carry out the desired reaction, showed a significant decrease when activated to 667° C. as compared to only 400° C.

EXAMPLE 4

SAPO-5 was activated by heating to 95° C. for 4 hours then to 390° C. at 2°/min and holding for 4 hours. Reactor conditions were established as in Examples 1–3 above. The results are reported in Table 5 below.

TABLE 5

| Alkylation of Aniline with Propylene over SAPO-5 Activated to 390° C. | | | | | | | | |
|---|---|---|---|---|---|---|---|---|
| Temp | P | | LHSV × | | SELECTIVITY (mole %) | | | Activity × |
| (°C.) | (psig) | N/R | 10³ | Conv | N—Alk | o-Alk | p-Alk | 10³ |
| 252 | 887 | 0.20 | 2.74 | 83.9 | 9.5 | 83.8 | 6.6 | 5.00 |
| 252 | 892 | 0.20 | 2.74 | 83.9 | 9.2 | 83.8 | 6.7 | 5.00 |
| 250 | 915 | 0.50 | 2.74 | 71.6 | 7.9 | 85.5 | 6.5 | 3.44 |

As can be seen from Table 5, while the activity of the SAPO-5 catalyst under these conditions was lower than the other catalysts tested, the ortho-selectivity of the reaction improved to over 83%.

EXAMPLE 5

SAPO-11 was activated by heating to 400° C. and holding for four hours. The alkylation reaction was carried out under the same conditions as for the previous examples. The results are reported in Table 6 below.

TABLE 6

| | | Alkylation of Aniline with Propylene over SAPO-11 | | | | | | |
|---|---|---|---|---|---|---|---|---|
| Temp (°C.) | P (psig) | N/R | LHSV × $10^3$ | Conv | SELECTIVITY (mole %) | | | Activity × $10^3$ |
| | | | | | N—Alk | o-Alk | p-Alk | |
| 252 | 935 | 0.5 | 2.74 | 14.8 | 33.9 | 63.3 | 2.3 | 0.44 |
| 251 | 933 | 0.5 | 2.74 | 15.3 | 34.1 | 63.2 | 2.6 | 0.44 |

The alkylation of aniline with propylene over SAPO-11, an aluminophosphate with a 6Å pore size, did not show the degree of activity of the other SAPO compositions, but the selectivity to ring alkylated products was still quite high; i.e., 63% ring alkylation selectivity is high for only a 15% conversion.

EXAMPLE 6

The process of Example 5 was carried out using isopropoanol as the alkylating agent. The reaction conditions were those set out above. The results of this example are reported in Table 7 below.

TABLE 7

| | | Alkylation of Aniline with isopropanol over SAPO-5 | | | | | | |
|---|---|---|---|---|---|---|---|---|
| Temp (°C.) | P (psig) | N/R | LHSV × $10^3$ | Conv | SELECTIVITY (mole %) | | | Activity × $10^3$ |
| | | | | | N—Alk | o-Alk | p-Alk | |
| 300 | 965 | 0.5 | 5.48 | 43.4 | 44.0 | 42.3 | 12.0 | 1.55 |
| 300 | 965 | 0.5 | 5.48 | 44.1 | 45.8 | 40.4 | 12.1 | 1.60 |

The results in Table 7 show that the alkylation of aniline with isopropanol does occur, although at a lower rate than with olefins. This lower activity with alcohols is consistent with the general trend with acidic catalysts. The ring alkylation selectivity is also lower than that found for alkylations with olefins, but this effect could be due to the presence of water in the feed from the dehydration of the alcohol.

EXAMPLE 7

Aniline was alkylated with propylene under the same reaction conditions as Example 4 above, except ALPO-5 was used as the catalyst. The results of this are set out in Table 8 below.

TABLE 8

| | | Alkylation of aniline with propylene over ALPO-5. | | | | | | |
|---|---|---|---|---|---|---|---|---|
| Temp (°C.) | P (psig) | N/R | LHSV × $10^3$ | Conv | SELECTIVITY (mole %) | | | Activity × $10^3$ |
| | | | | | N—Alk | o-Alk | p-Alk | |
| 250 | 886 | .20 | 8.22 | 83 | 9.9 | 84.4 | 4.9 | 14.6 |
| 250 | 888 | .20 | 8.22 | 83 | 10.0 | 83.0 | 4.7 | 14.6 |

The ALPO-5 catalyst exhibited the best combination of activity and O-alkylation selectivity of all the catalysts tested for the alkylation of aniline with propylene.

EXAMPLE 8

The procedure of Example 7 above was repeated substituting MAPO-36 for ALPO-5 as the catalyst. The results are reported in Table 9 below.

TABLE 9

| | | Alkylation of aniline with propylene over MAPO-36. | | | | | | |
|---|---|---|---|---|---|---|---|---|
| Temp (°C.) | P (psig) | N/R | LHSV × $10^3$ | Conv | SELECTIVITY (mole %) | | | Activity × $10^3$ |
| | | | | | N—Alk | o-Alk | p-Alk | |
| 250 | 922 | .20 | 2.74 | 5 | 18.1 | 80.0 | 2.0 | .14 |
| 250 | 911 | .20 | 2.74 | 4.4 | 18.1 | 80.0 | 2.0 | .14 |

The activity of MAPO-36 Catalyst was low, but the ortho-alkylation selectivity was 80%, indicating that MAPO-36 may be a suitable catalyst for reactions when selectivity is the primary concern.

EXAMPLE 9

Aniline was alkylated with isobutylene under the conditions of Example 7 above using ALPO-5 as the catalyst. The results are reported in Table 10 below.

TABLE 10

| | | Alkylation of Aniline with Isobutylene over ALPO-5 | | | | | | |
|---|---|---|---|---|---|---|---|---|
| Temp (°C.) | P (psig) | N/R | LHSV × $10^3$ | Conv | SELECTIVITY (mole %) | | | Activity × $10^3$ |
| | | | | | N—Alk | o-Alk | p-Alk | |
| 180 | 568 | .67 | 2.74 | 34 | 1.9 | 61.7 | 35.7 | 1.13 |
| 180 | 566 | .67 | 2.74 | 27 | 3.1 | 62.0 | 32.5 | 0.86 |

N—alk = N—t-butylaniline
O—alk = 2-t-butylaniline
p-alk = 4-t-butylaniline + 2,4 di-t-butylaniline Alkylation with isobutylene over ALPO-5 did not exhibit activities or selectivities as goods as when propylene is used as the alkylating agent, but did exhibit satisfactory results for the alkylation reaction.

As can be seen from the results reported above, the class of aluminophosphate catalysts of the present invention generally exhibit high catalyst activity as well as high ortho-alkylation selectivity. In many cases the activity and/or selectivity is superior to that exhibited by zeolitic molecular sieve catalysts. Additionally, the non-zeolitic molecular sieve catalysts described above are generally more thermally stable than the zeolite materials used for aromatic amine alkylation.

Having thus described the present invention, what is now deemed appropriate for Letters Patent is set out in the following appended claims.

What is claimed:

1. In a process for alkylating aromatic monoamines to selectively produce ortho-alkylated products by reacting said monoamines with an alcohol, olefin or diolefin under reaction conditions suitable for carrying out said alkylation, the improvement which comprises: carrying out said alkylation in the presence of a non-zeolitic, molecular sieve catalyst having micropores sufficiently large to allow the reactants to diffuse into said mircopores and products to diffuse out.

2. The process according to claim 1 wherein said non-zeolitic molecular sieve is a crystalline aluminophosphate catalyst.

3. The process according to claim 1 wherein the non-zeolitic molecular sieve is a crystalline silicoaluminophosphate catalyst.

4. The process according to claim 1 wherein said non-zeolitic molecular sieve is a crystallne metalloaluminophosphate catalyst.

5. The process according to claim 1 wherein said non-zeolitic molecular sieve has an average micropore diameter of at least 6 Å as measured by the absorption of probe molecules.

6. The process in accordance with claim 1 wherein said aromatic amine is selected from the group consisting of aniline, toluidines, and dimethylanilines.

7. The process in accordance with claim 1 wherein said aliphatic alcohol is a straight chain or branched $C_{1-10}$ alcohol.

8. The process in accordance with claim 1 wherein said aliphatic olefin is a halogen-substituted or unsubstituted, straight chain or branched $C_{2-10}$ olefin.

9. The process in accordance with claim 1 wherein said alkylation is carried out at a temperature range between 25° C. and 350° C.

10. The process in accordance with claim 1 wherein said alkylation is carried out at a pressure range between 14.7 and 2000 psia.

11. The process in accordance with claim 2 wherein said crystalline aluminophosphate is ALPO-5.

12. The process in accordance with claim 3 wherein said crystalline silicoaluminophosphate is SAPO-5.

13. The process in accordance with 3 wherein said crystalline silicoaluminophosphate is SAPO-37.

14. The process in accordance with claim 4 wherein said crystalline metalloaluminophosphate is MAPO-5.

15. The process in accordance with claim 4 wherein said crystalline metalloaluminophosphate or aluminophosphate is impregnated with a metal of Group 1 to 15.

16. The proess in accordance with claim 8 wherein the molar ratio of olefin to aromatic amine is from about 0.5 to 10.

* * * * *